US005090796A

United States Patent [19]
Feinbloom

[11] Patent Number: 5,090,796
[45] Date of Patent: Feb. 25, 1992

[54] TEST FRAME FOR FITTING A PATIENT WITH TELESCOPIC CORRECTIVE LENSES AND ASSOCIATED METHOD

[75] Inventor: Richard E. Feinbloom, New York, N.Y.

[73] Assignee: Designs for Vision, Inc., Ronkonoma, N.Y.

[21] Appl. No.: 617,670

[22] Filed: Nov. 26, 1990

[51] Int. Cl.⁵ ............................................. G02C 1/00
[52] U.S. Cl. ..................................... 351/158; 351/41
[58] Field of Search ............... 351/41, 57, 58, 59, 351/158; 350/145, 146

[56] References Cited

U.S. PATENT DOCUMENTS 4,364,645 12/1982 Feinbloom ...................... 351/158

Primary Examiner—Rodney B. Bovernick
Attorney, Agent, or Firm—Arthur L. Plevy

[57] ABSTRACT

An apparatus and a method for assisting in the selection of corrective lenses includes a spectacle frame having at least one test mounting lens emplaced in the eyepiece of the frame. The test mounting lens has a horizontally elongated aperture for releasably and slideable receiving a telescope holder therein. The telescope holder releasably retains a telescope within it and rides in the slot for positioning the telescope in a position that allows a person being tested to see through the telescope. The method includes placing a telescope of a selected optical strength in an apparatus having a telescope holder; placing the apparatus on a person to be tested in the way that spectacles are worn; adjusting the position of the telescope so that the person can look through it; replacing the telescope initially placed in the telescope holder with telescopes of a different optical strength and permitting the person to view through them; and repeating this step until the person ascertains the telescope that provides the best vision correction.

18 Claims, 2 Drawing Sheets

TEST FRAME FOR FITTING A PATIENT WITH TELESCOPIC CORRECTIVE LENSES AND ASSOCIATED METHOD

FIELD OF THE INVENTION

The present invention relates to an eyeglass test frame to be used for fitting a patient with corrective optical lenses, and more particularly to an adjustable test frame which allows a patient with severe vision impairment to try a variety of telescopic lens for suitability, as well as, simultaneously sample from a selection of carrier lens.

DESCRIPTION OF THE PRIOR ART

A variety of equipment for fitting a patient with corrective optical lenses is known. Essentially, these various devices utilize a common overall method, viz., a patient needing corrective lenses is placed in a controlled visual environment, e.g., seated at a fixed distance from an eyechart, a variety of lenses is sequentially positioned before the patient's eyes, and the patient subjectively determines which lenses provide the best vision.

This process of lens selection is complicated somewhat in the case of the severely visually impaired. In order to correct severe impairment, telescopic lenses fitted to the lenses of conventional eyeglasses are now commonly used, see, e.g., the catalog of Designs for Vision, Inc. of Ronkonkoma, N.Y. Conventional eyeglass lenses, when used for holding telescopes, such as by mounting the telescopes in bores made through the lenses, are denominated "carrier lenses". The carrier lenses may or may not be optically corrective, and thus may do more than simply "carry" the telescopes.

Telescopic lenses exhibit a degree of magnification unattainable by single lens systems, but due to their high magnification, have a small field of view, and thus the image seen through them is quite sensitive to the angle of latitudinal and longitudinal inclination, i.e., the pantoscopic or retroscopic tilt, of the telescope axis. Redirection of telescope position by even one degree can result in the visualization of a totally different image through the telescope. This is particularly significant with regard to stereoscopic viewing. It is, of course, desirable for an optical aid to produce an integrated stereoscopic image which approximates normal sight. In the instance of a dual telescopic system, the telescopes should be focused on the same field of view, much as binoculars typically focus, i.e., they should exhibit "binocularity". The focusing of two telescopes upon the same field of view requires a holding device which permits the telescopes to be closely aligned relative to each other, i.e., approximately parallel in most cases. Further, in order for a patient to look through the telescopes at all, they must be positioned accurately in his line of sight. With dual telescopic systems, each telescope must be positioned in the line of sight of a corresponding eye. The spacing between the eyes, or interpupillary distance, varies with the individual patient, and thus the telescope holding device must be adjustable to accommodate varying interpupillary distances.

The general requirements for telescopic corrective lens systems are applicable to test frames for fitting patients with telescopic lenses, in that the selection of the best telescopic lenses for a patient's needs must be based upon a comparison of a variety of telescopes held in the test frame so that any given pair are properly positioned in the patient's line of sight and preferably are focused on a common visual field.

An example of a test frame for accommodating telescopic lenses is shown in U.S. Pat. No. 4,364,645 entitled ADJUSTABLE FRAME APPARATUS FOR TELESCOPIC SPECTACLES issued Dec. 21, 1982 to William Feinbloom, the Inventor herein.

In addition to the selection of telescopes in a telescopic corrective lens appliance, the lenses in which the telescopes are installed, i.e., the carrier lenses, are frequently part of the patient's prescription. For example, the carrier lenses may provide vision for close observation with the telescopes allowing distant visualization. It is desirable, in the process of fitting a patient with a telescope/carrier lens corrective lens system, to duplicate the combination of carrier lens and telescope lens that will ultimately be made for the patient, rather than to select the lenses totally independently and without the opportunity to experience their use in a complete system. The duplication of the combination allows the patient to experience exactly what the combination that he will receive from the optician will be like, before it is made.

In working with the severely visually handicapped, it is frequently the case that a corrective lens system must be selected which is usable only over certain ranges of distance, i.e., a full range of visual capability can not be achieved through the use of the limited set of corrective lens which may be practically carried on a single appliance. The patient is therefore presented with certain limited options from which he must select. If a variety of combinations of carrier lens and telescopes can be presented to the patient, he can make an informed selection based upon actual experience.

Presently, there is no single device which allows a partially sighted patient to contemporaneously sample from a selection of telescopic lenses and carrier lenses. There is no simple device which permits universally rotatable telescopes to be sampled.

The test frames used today are typically large and cumbersome and are only appropriate for examinations conducted in the practitioner's office. This is not particularly suitable to the severely visually handicapped or partially sighted person who has difficulty in travelling to the practitioner's office. It is therefore an object of the present invention to provide a portable test frame which permits the fitting of a patient with telescopic corrective lenses in the field, e.g., in the patient's home.

It is a further object of the present invention to provide a test frame system which is compact and readily stored, which is relatively simple to manufacture and of modest cost, thereby making the fitting of telescopic corrective lenses cheaper and hence more accessible to more persons.

SUMMARY OF THE INVENTION

The problems and disadvantages associated with the conventional techniques and devices utilized for assisting a partially sighted person in selecting corrective lenses are overcome by the present invention which includes both an apparatus and a method for assisting in the selection of corrective lenses. The apparatus includes a spectacle frame having at least on test mounting lens emplaced in the eyepiece of the frame. The test mounting lens has a horizontally elongated aperture for releasably and slideable receiving a telescope holder therein. The telescope holder releasably retains a telescope within it and rides in the slot for positioning the telescope in a position that allows a person being tested to see through the telescope. The method includes placing a telescope of a selected optical strength in an apparatus having telescope holding means; placing the apparatus on a person to be tested in the way that spectacles are worn; adjusting the position of the telescope so that the person can look through it; replacing the telescope initially placed in the telescope holder with telescopes of a different optical strength and permitting the person to view through them; and repeating this step until the person ascertains the telescope that provides the best vision correction.

BRIEF DESCRIPTION OF THE FIGURES

For a better understanding of the present invention, reference is made to the following detailed description of an exemplary embodiment considered in conjunction with the accompanying drawings, in which.

DETAILED DESCRIPTION OF THE FIGURES

Figure 1:
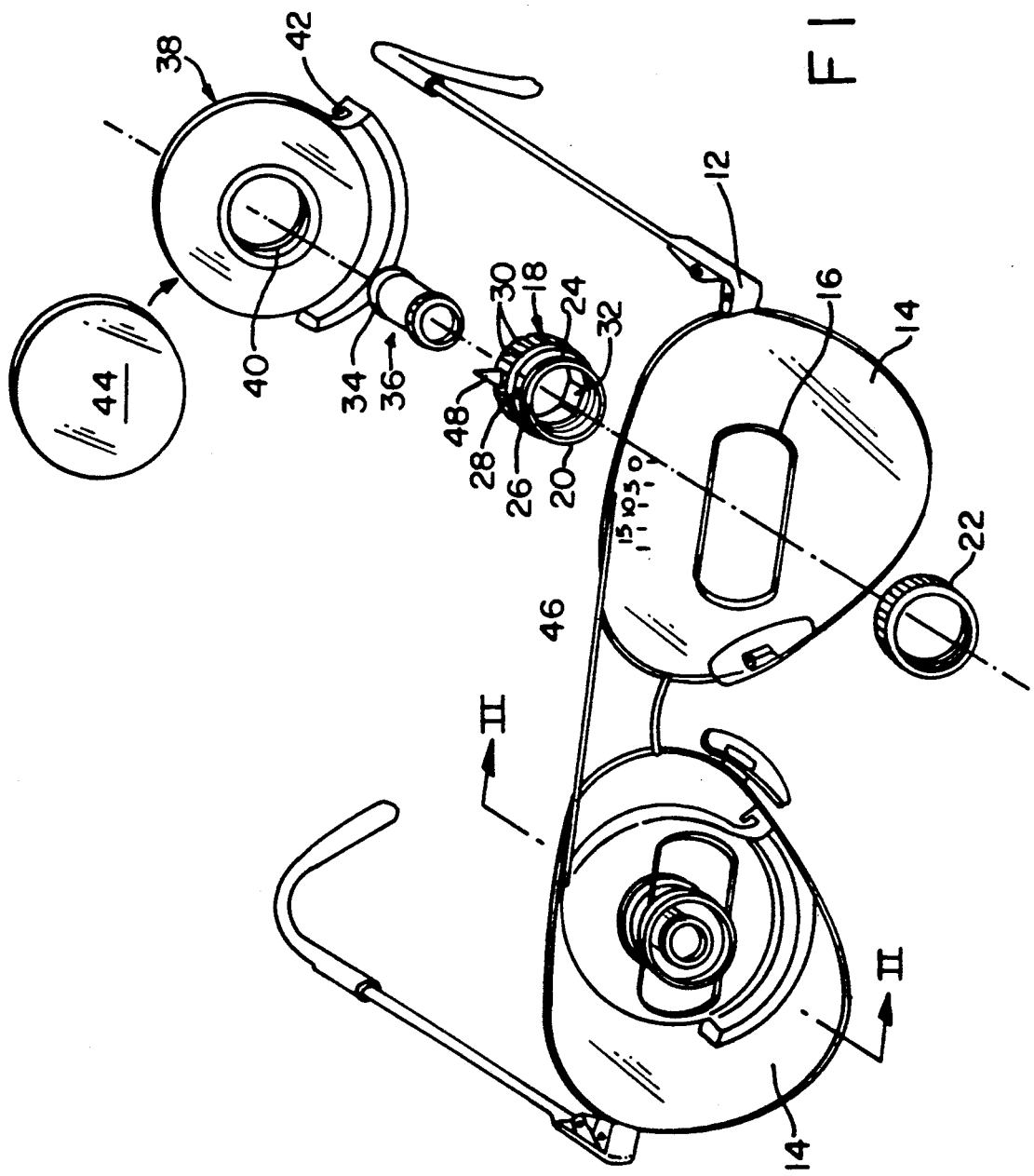
FIG. 1 is a partially exploded perspective view of a test frame in accordance with an exemplary embodiment of the present invention.
Figure 2:
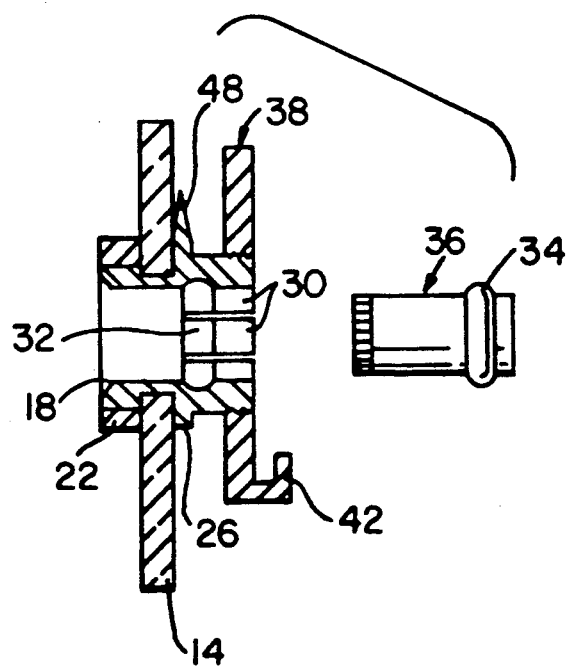
FIG. 2 is a cross-sectional view of the test frame illustrated in FIG. 1 taken along section line II—II and looking in the direction of the arrows.

Referring to FIGS. 1 and 2, a test frame assembly 10 in accordance with an exemplary embodiment of the present invention is shown. A sturdily constructed conventional eyeglass frame 12, as is commonly used by persons needing prescription eyeglasses, receives therein a pair of testing (test mounting) lenses 14. The testing lenses 14 are clear, have no optical strength, and are preferably constructed from glass or a tough polymeric compound, as is commonly used in making lenses for eyeglasses. The testing lenses 14 each have an elongated slot 16 for receiving therein a collet 18. The collet 18 has a threaded front nipple 20 which slips through the slot 16 and receives thereon an internally threaded ring 22. The collet 18 has a land 24 disposed intermediate the nipple 20 and a retaining flange 26. The land 24 has at least one pair of flats 28 formed in its outer periphery and disposed opposite one another. The opposite surfaces of the flats 28 are spaced at a distance approximating the width of the elongated slot 16 so that the flats 28 just clear the slot and prevent the collet 18 from being turned in the slot. The flats 28 thus permit the threaded ring 22 to be twisted onto the nipple 20 to retain the collet 18 within the slot 16 by capturing the testing lens 14 between the ring 22 and the retaining flange 26. A plurality of flexible fingers 30 project from the collet 18 opposite to the nipple 20 forming, in effect, an expandable cylinder. Proximate the base of the fingers 30 and internal to the collet 18, a partial spheric socket 32 is formed. The socket 32 rotatably receives therein a mating toroidal collar 34 disposed around the outer periphery of a telescope 36. The telescope 36 is fitted to the collet 18 by insertion into the expandable cylinder formed by the flexible fingers 30 and pressing it through the collet 18 until the collar 34 bottoms out against the socket 32. Once the telescope 36 is positioned fully within the collet 18, a sample lens holder 38 having an internal bore 40 therethrough may be placed over the cylinder formed from flexible fingers 30 which are threaded on their exterior surface. When the lens holder 38 is tightened upon the flexible fingers 30 the collar 34 of the telescope 36 is captured snugly within the socket 32 preventing inadvertent withdrawal therefrom and permitting stable positioning of the telescope 36 under finger pressure. The dimensions of the various aforementioned parts may be adjusted to result in a gradually increasing frictional embracing of the collar 34 by the socket 32 upon additional tightening of the sample lens holder 38. The sample lens holder 38 has a ledge 42 formed along a portion of its periphery to securely but removably accommodate a sample prescription carrier lens 44 that is placed therein to allow the patient to experience the visual effect of the lens. The carrier lenses worn by partially sighted persons usually have a high degree of curvature, i.e., small radius of curvature, and therefore are sensitive to proper centering relative to the pupil of the patient who wears them. In order for a patient to accurately test a carrier lens for corrective effect, it is important therefore, that the lens be properly aligned in his line of sight, much as the telescopes 36 previously mentioned. This requirement is conveniently met by the present invention in that the telescope position may be ascertained by adjustment of the collets 18 within the slots 16 and locked in place by tightening the threaded rings 22. The sample lens holders 38 are thereby automatically positioned by the adjustment of the collets 18 for positioning the telescopes 36. Thus when the sample prescription carrier lenses 44 are placed in the sample lens holder 38, they are properly positioned relative to the patient's eyes. It is intended that the telescopes 36 are to installed in the carrier lenses in the finished appliance by insertion into bores in the carrier lenses. As is the common practice, the appropriate combination of carrier lenses and telescopes for a patient can be ascertained with the present invention either by selecting the telescopes 36 and then selecting the carrier lenses after the telescopes are centered. The sample lens holder 38 is arranged so that it is aligned with the optical axis of the telescope. Hence aperture 40 of the carrier 38 is coaxial with the telescope. The lens 44 accordingly is also optically aligned. Hence the patient can now view through the corrective lens 44 and the telescope 36. By moving his eye the patient can also view through the corrective lens 44. A reference scale 46 imprinted on or embossed into the testing lens 14 proximate the slot 16 can be employed for quantifying and recording the interpupillary distance pertaining to the patient being examined. A pointer tab 48 protruding from the outer peripheral edge of the retaining flange 26 can serve to indicate the position of the collet 18 with respect to the reference scale 46.

It should be seen from the aforegoing description that a sampling of telescopes and/or carrier lenses by the patient may be readily accomplished by use of the present invention. It should be further understood that the embodiments described herein are merely exemplary and that a person skilled in the art may make many variations and modifications without departing from the spirit and scope of the invention as defined in the appended claims.

I claim:

1. A testing apparatus for assisting a partially sighted person in selecting corrective lenses comprising:
   A) a spectacle frame having at least one test mounting lens emplaced in the eyepiece of said frame said test mounting lens including horizontally elongated slot for releasably and slideable receiving therein
   B) telescope holding means for releasably retaining a telescope therein, said telescope holding means riding in said slot for positioning said telescope in a position that allows said person to see through said telescope, and sample lens holding means coupled to said telescope holding means for releasably holding a sample carrier lens in a position that allows said person to see through said sample carrier lens and said telescope with said telescope an sample carrier lens positioned on the same optical axis.

2. The apparatus of Claim further including first locking means for releasably locking said telescope holding means at a selected position in said slot.

3. The apparatus of Claim 2, wherein said telescope holding means includes second locking means for releasably locking said telescope within said telescope holding means.

4. The apparatus of Claim 3, wherein said telescope holding means includes a socket internal thereto for receiving a mating collar disposed about the exterior peripheral surface of said telescope.

5. The apparatus of Claim 4, wherein said socket and said collar are each at least partially spheric, whereby a ball and socket joint is formed therebetween permitting said telescope to be positioned at a variety of positions within a conic shaped range.

6. The apparatus of Claim 5, wherein said second locking means releasably locks said telescope at a selected position within said conic shaped range.

7. The apparatus of Claim 6, wherein said telescope holding means is a generally cylindrical collet having an threaded front nipple for projecting through said elongated slot and a flange disposed peripherally around said collet distal to said front nipple, said flange preventing said collet from passing through said slot, said locking means including said front nipple and a threaded ring received thereon capturing said test mounting lens between said threaded ring and said flange.

8. The apparatus of Claim 7, wherein said collet includes a plurality of flexible fingers protruding from one end of said collet distal to said front nipple and parallel to the wall of said generally cylindrical collet, said fingers bearing threads on an exterior surface to form a discontinuous threaded nipple for receiving thereon a threaded lock ring, said fingers on a side opposite to the threads and proximate the origin of said fingers on said collet forming at least a portion of said socket, said second locking mean including said fingers and said threaded lock ring, said fingers deflecting inwardly towards the axis of said collet when said lock ring is screwed on said discontinuous nipple pressing a portion of said socket into said mating collar.

9. The apparatus of Claim 8, wherein said sample lens holding means is a substantially planar member having an approximately centrally disposed threaded bore therethrough and a rim with an L-shaped lip which at least partially but not completely surrounds said member peripheral edge, said threaded bore being received upon said discontinuous nipple for deflecting said fingers into said collar.

10. The device of Claim 9, further including measuring means for measuring and recording the interpupillary distance of said person determined by positioning a pair of said telescopes at a position through which said person can see through said pair of telescopes.

11. The device of claim 10, wherein said sample carrier lenses are penetrated by a bore through which said telescope images may pass undisturbed to the eyes of said patient when said telescopes are held in said telescope holding means and said sample lenses are held in said sample lens holding means.

12. A method for assisting a partially sighted person in selecting corrective lenses utilizing a testing apparatus having a spectacle frame with at least one test mounting lens emplaced in the eyepiece of said frame, said test mounting lens including a horizontally elongated slot for releasably and slideable receiving therein a telescope holding means for releasably retaining a telescope therein, and a sample lens holding means for releasably retaining a sample carrier lens therein, said telescope holding means riding in said slot for positioning said telescope and said sample carrier lens in a position that allows said person to see through said sample carrier lens and said telescope and comprising the steps of:

A) placing a telescope of a selected optical strength in said telescope holding means;

B) placing a sample carrier lens of a selected optical strength in said sample lens holding means;

C) placing said apparatus of the person to be tested in the way that spectacles are worn;

D) adjusting the position of said telescope and said sample carrier lens so that the person can look through it;

E) repeating steps A and B until the patient ascertains which sample carrier lens and telescope combination provides the best optical correction.

13. The method of claim 12, further comprising repeating steps A through E of claim 12 to ascertain a proper telescopic corrective lens for the patient's other eye.

14. The method of claim 13, wherein said testing apparatus includes locking means for releasably locking said telescope holding means at a selected position in said slot and further including the step of locking said telescope holding means position after said step of adjusting the position of said telescope so that the person can look through it.

15. The method of claim 14, wherein said telescope holding means includes a spherical socket internal thereto for receiving a mating collar disposed about the exterior peripheral surface of said telescope, whereby a ball and socket joint is formed therebetween permitting said telescope to be positioned at a variety of positions within a conic shaped range and wherein the step of positioning the telescope so the person see through it includes the step of A) rotating said telescope upon said ball and socket joint to position the axis of said telescope in a position which permits the person being tested to look through said telescope.

16. The method of claim 14, further comprising repeating the steps of claim 12 to ascertain a proper telescopic corrective lens for the patient's other eye.

17. The method of claim 15, wherein said apparatus includes measuring means for measuring and recording the interpupillary distance of said person determined by positioning a pair of said telescopes at a position through which said person can see through said pair of telescopes and further including the steps of measuring and recording the interpupillary distance of the person being tested.

18. The method of claim 17, further including the step of removing said telescope from said telescope holding means prior to looking through said sample carrier lens.

* * * * *